United States Patent
Erickson

(10) Patent No.: US 6,725,893 B1
(45) Date of Patent: Apr. 27, 2004

(54) COVER ASSEMBLY FOR A CRASH CART

(76) Inventor: Tomiko Erickson, 10100 E. Calusa Club Dr., Miami, FL (US) 33186

( * ) Notice: Subject to any disclaimer, the term of this patent is extended or adjusted under 35 U.S.C. 154(b) by 0 days.

(21) Appl. No.: 10/052,996

(22) Filed: Jan. 18, 2002

Related U.S. Application Data

(60) Provisional application No. 60/296,704, filed on Jun. 7, 2001.

(51) Int. Cl.$^7$ ............................ B65D 65/18; B65D 65/22
(52) U.S. Cl. ........................................ 150/154; 150/165
(58) Field of Search ................................. 150/154, 166; 312/6; 128/849; 296/100.1; 280/655.1, 651

(56) References Cited

U.S. PATENT DOCUMENTS

| | | | | |
|---|---|---|---|---|
| 2,917,094 A | * | 12/1959 | Sullivan | 150/166 |
| 4,538,385 A | * | 9/1985 | Kandarian | 150/154 X |
| 4,741,167 A | * | 5/1988 | Wigley | 312/6 X |
| 4,782,873 A | * | 11/1988 | Messner et al. | 150/154 |
| 4,948,154 A | * | 8/1990 | Guggenheim | 150/154 X |
| 4,954,384 A | * | 9/1990 | Hartwell | 150/154 X |
| 5,192,092 A | * | 3/1993 | DiBenedetto | 150/154 X |
| 5,429,142 A | * | 7/1995 | Szabo et al. | 128/849 |
| 5,524,643 A | * | 6/1996 | Faries, Jr. et al. | 128/849 |
| 5,772,293 A | * | 6/1998 | Hughes | 312/7.2 X |
| 6,188,450 B1 | * | 2/2001 | Coons | 384/841 |
| 6,209,973 B1 | * | 4/2001 | Steinberg | 312/7.2 |

* cited by examiner

*Primary Examiner*—Sue A. Weaver
(74) *Attorney, Agent, or Firm*—Malloy & Malloy, P.A.

(57) ABSTRACT

A cover assembly for a hospital crash cart constructed of a clear, flexible material to permit medical personnel to view the equipment and supplies included on the crash cart without removing the cover. The cover is structured to minimize contamination of the equipment and supplies by reducing exposure to dirt, dust, bacteria, or other airborne or contact contaminants. The cover includes a plurality of apertures which are normally disposed in a closed orientation by fasteners, such as, for example, hook and loop type fasteners. At least one release aperture is provided so that the cover may be quickly and easily removed from the crash cart. In one embodiment the cover assembly includes additional apertures to permit access to an electronic display monitor, electrical connections, and crash cart handles. The cover also includes at least one adjustable portion, and a pouch attached to an exterior surface of the cover.

15 Claims, 3 Drawing Sheets

COVER ASSEMBLY FOR A CRASH CART

The present application is based on and a claim of priority is made pursuant to 35 U.S. Section 119(e) to the prior filed, provisional patent application with a filing date of Jun. 7, 2001 and having Ser. No. 60/296,704.

BACKGROUND OF THE INVENTION

1. Field of the Invention

The present invention relates to a cover assembly for a multi-purpose, mobile, utility cart, commonly known as a "crash cart," which is generally used in hospitals or similar medical facilities to quickly and easily transport a variety of equipment and supplies in a medical emergency.

2. Description of the Related Art

The use of a multi-purpose, mobile utility cart in a hospital or similar environment to quickly and easily transport equipment and supplies in a medical emergency is well known. This type of cart, commonly known as a "crash cart," is necessitated by the fact that in a medical emergency, response time is critical. Therefore, hospitals and other types of medical facilities frequently utilize a cart equipped with multiple shelves and/or storage compartments, and which is movably supported on wheels or casters, to permit quick and easy transport of medical equipment and supplies to an area where they are required.

A "crash cart" is utilized to contain, support and transport a variety of medical equipment and supplies to a location, wherever they may be required. The equipment and supplies range from highly technical equipment such as, for example, heart defibrillators, electronic monitoring devices or electronic monitoring screens associated with one or more computers, to more common items including intravenous treatment supplies, respiration masks, oxygen supply tanks, syringes, bandages, and medication. The variety of equipment and supplies included on a crash cart permit medical personnel to quickly respond to common medical emergencies including, for example, a heart attack, stroke, and/or trauma, which occur with some frequency in a hospital or similar medical facility.

Although a crash cart provides a quick and easy means to transport required medical equipment and supplies in a medical emergency, there is room for concern with regard to the sanitation of the equipment and supplies included on a crash cart. First, because a crash cart is designed to be mobile throughout most, if not all, areas inside and outside of a hospital or similar facility, the equipment and supplies included on a crash cart are likely to be exposed to perhaps more than just a small amount of dust, dirt, blood, bacteria, and other potential germ sources, whereas medical equipment which is permanently stationed in an area is not as likely to be so exposed. Further, because crash carts are often stationed at locations around a hospital facility for ready access by medical personnel, they are also readily accessible to non-medical personnel who may inadvertently contaminate the equipment or supplies by handling, removing, dropping and/or replacing items on the crash cart, not to mention sneezing and/or coughing around such items. Also, due to the delicate nature of some equipment, and the hazardous nature of others, access by unauthorized personnel is generally not acceptable. Accordingly, it would be beneficial if there were an assembly or other means of ensuring that a crash cart and/or the equipment carried on one are at least reasonably sanitary. If any such assembly were developed, it would preferably be relatively simple to implement and use such that a time consuming procedure would not have to be followed for its use. Simply put, without an efficient and effective means to assure proper sanitation, the often life saving advantages of crash carts may be diminished, and possibly lost, if medical personnel are hesitant to use them due to concerns about the proper sanitation of the equipment and supplies included thereon.

It is believed that in some hospitals, it is possible to observe the placement of a tarpaulin or similar, standard type of cover over a crash cart in an attempt to protect them from dust, and possibly other contaminants, while not in use. However, these types of standard covers are typically made of an opaque material which can result in the loss of valuable time in an emergency situation as medical personnel may not readily identify the covered object as a crash cart. In addition, even if identified as a crash cart, valuable time may still be lost due to medical personnel uncovering the cart to verify that it contains the specific equipment they require in an emergency. Therefore, a need exists in this field for a cover assembly which permits medical personnel to view the crash cart without removing the cover. Moreover, it is possible that the placement of a tarpaulin or other type of standard cover on a crash cart may hamper accessibility to the equipment and supplies included on the cart in an emergency. Thus, a need also exists for a cover assembly for a crash cart which may be quickly and easily removed to allow access to equipment and supplies in a medical emergency or which readily facilitates access to such equipment in the first place.

In addition, tarpaulins and similar standard covers typically have a generally rectangular configuration which when draped over a crash cart, leaving an opening at or near the bottom only, and this presents additional problems with regard to the mobility and maintenance of the crash cart. For example, a crash cart often contains electrical equipment which requires a connection to an electrical source either for operation or maintenance of a charge on portable electronic equipment or a portable power supply. However, tarpaulins and similar standard covers are not designed to accommodate an electrical connection to the covered object. Thus, it would be desirable if any new cover assembly for a crash cart were to include an opening specifically designed to permit electrical connections to be made there through. Also, there are many crash carts which carry an electronic video display monitor and/or computer associated therewith, either or all of which usually needs to be accessed daily to perform diagnostic tests on the equipment included on the cart. As such, it would be preferable to provide a cover assembly for a crash cart which permits access to the electronic display monitor and/or computer without uncovering the entire crash cart.

In addition, the use of tarpaulins and similar standard types of covers may hamper the ability of medical personnel to properly grip the handles provided on many crash carts, as necessitated during its being transported to the location of an emergency, without at least partially removing the cover. As noted above, however, the movement of a crash cart though the hospital, or similar facility, is one of the sources of potential contamination to the equipment and supplies included on the crash cart. Thus, it would also be desirable to provide a cover assembly for a crash cart which allows access to the handles without removal of the cover.

Accordingly, there remains a need in this field of art for a cover assembly to be used with a "crash cart" or similar type of utility cart, which can be, but does not have to be, quickly and easily removed, and further, which allows the equipment and supplies included on the cart to be viewed, while the cover assembly remains in place over the cart. If any such cover assembly were developed, it would be beneficial to permit easy access to and operation of an electronic video display monitor carried on the crash cart, including any computer associated therewith, and an interconnection to an external power supply, while the cover remains in place over the cart. Any such cover assembly would preferably also be structured to readily permit accessibility to the handles of the cart while the cover remains in place over the cart in order that these may be gripped directly for facilitating the cart's being transported within a hospital to the site needed in an emergency, and further, to permit quick and easy adjustment to assure a proper fit of the cover over the equipment and supplies included on the crash cart.

SUMMARY OF THE INVENTION

The present invention is intended to address these and other needs which remain in the art and is directed to a cover assembly for multi-purpose, mobile, utility carts, and in particular, to carts commonly known as "crash carts," which are often used in hospitals to resuscitate a heart attack victim, among other uses. Crash carts are intended to provide a quick and easy means to transport equipment and supplies throughout a hospital or similar medical type of facility, and given their mobility and need to be instantly accessible, are more apt to come in contact with dust, bacteria and other germs.

The cover assembly of the present invention includes a cover having a main body portion and an adjustable portion, and in one embodiment, a monitor portion as well. The cover assembly is further structured and disposed so that it is position able in an overlying relationship with the crash cart, at least partially defined by the cover surrounding the top, front, rear, and sides of the crash cart. The cover is preferably at least partially constructed of a clear, flexible, tear and puncture resistant material so that the equipment and supplies on the cart are visually observable while the cart is covered, and has sufficient flexibility so as to be easily adjustable to accommodate the various combinations of equipment and supplies typically included on a crash cart. One preferred embodiment of the present invention comprises a heavy gauge, clear, vinyl or plastic, although its construction is not limited to this type of material.

The cover assembly of the present invention further comprises at least one, but preferably a plurality of release apertures. The release apertures are preferably structured to extend in a generally vertical orientation originating at the bottom of the main body portion along a substantial section of its height, although could be structured differently. In the preferred embodiment, each release aperture is disposed in a normally closed orientation, and is retained in a closed orientation by at least one release fastener, when the fastener is engaged. The release fastener may comprise, by way of example only, a hook and loop fastener, button, snap, zipper, ties or other standard fastener. The release fasteners are ideally structured to allow the release aperture to be quickly and easily disposed into an open orientation to permit quick and easy removal of the cover from the crash cart when required in an emergency.

As described above, in one embodiment of the present invention the cover assembly includes a monitor portion to accommodate a video display monitor carried on the crash cart, and in this embodiment, the assembly preferably includes a release aperture in the nature of a monitor aperture that is cooperatively engaged with the monitor portion of the cover assembly, wherein the monitor aperture is normally disposed in a closed orientation by a monitor fastener. The monitor fastener may comprise any of the standard fasteners previously disclosed. The monitor aperture is designed to allow medical personnel to access and/or operate an electronic display monitor, without removing the cover from the crash cart.

In addition, the cover assembly of the present invention preferably includes a release aperture in the nature of at least one, but preferably a plurality of handle apertures. Each handle aperture is designed to permit a handle of the crash cart to extend through the cover while the cover is in an overlying relationship with the crash cart. The handle apertures are further structured to fit snug against or about the handles to minimize the accessibility for potential contaminants to reach the crash cart or items carried thereon.

The cover assembly of the present invention preferably also includes a release aperture in the nature of at least one electrical aperture which is disposed in a normally closed orientation by at least one electrical fastener. The electrical fastener may also comprise any of the standard fasteners previously disclosed. The electrical aperture is structured to permit a connection to an external electrical outlet from the equipment on the crash cart while the cover remains in place over the crash cart. In addition, the electrical aperture facilitates the electrical connection which is needed in order for diagnostic equipment tests, many of which require connection to an external power supply, to be performed while the cover remains disposed in an overlying relationship with the crash cart.

There are a number of different combinations of equipment and supplies which may be included on a crash cart, depending on its specific intended use, and, therefore, crash carts may vary in dimension from one to another. The cover assembly of the present invention may accordingly vary; larger or smaller dimensions may be provided. However, a proper or relatively snug fit between the cover assembly and the crash cart on which it is used should ideally be maintained to minimize air circulation inside the cover so as to minimize the potential for contamination of the equipment and supplies. To that end, the cover assembly of the present invention ideally also includes at least one adjustable portion, but preferably two adjustable portions. The at least one adjustable portion of this embodiment further comprises at least one retaining member structured and disposed to retain the adjustable portion in an at least partially collapsed orientation when operatively engaged.

The cover assembly of the present invention ideally also includes at least one pouch disposed on an exterior surface thereof. In one preferred embodiment, the pouch is sized to contain a standard medical chart. The pouch may include a flap, which may be secured with a pouch fastener. The pouch fastener may comprise any one of the standard fasteners previously disclosed above. The at least one pouch may instead be utilized to contain information about the equipment and supplies included on the cart or a separate pouch may be provided on the cover assembly for this purpose. This information may include, for example, an inventory of equipment and supplies, a log of diagnostic equipment tests required and/or performed, routine maintenance, supply restocking dates, or any other information deemed necessary by medical personnel.

The objects, features and advantages of the present invention will become more clear when the drawings as well as the following detailed description of the preferred embodiment(s) are taken into consideration.

BRIEF DESCRIPTION OF THE DRAWINGS

For a fuller understanding of the nature of the present invention, reference should be had to the following detailed description taken in connection with the accompanying drawings in which.

Like reference numerals refer to like parts throughout the several views of the drawings.

DETAILED DESCRIPTION OF VARIOUS PREFERRED EMBODIMENT(S)

Figure 1:
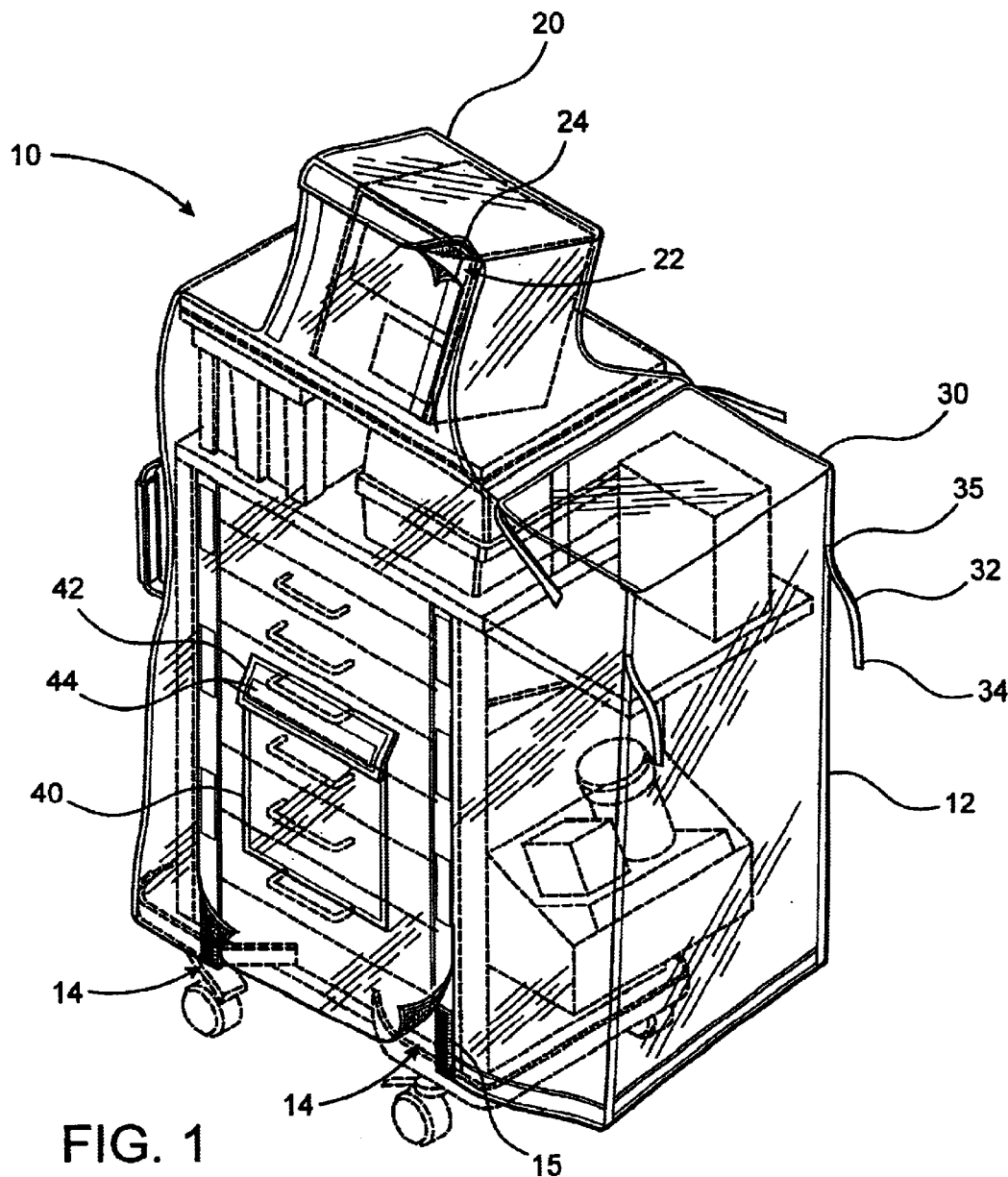
FIG. 1 is a front perspective view of a cover assembly according to the present invention in a first embodiment.

While this invention is susceptible of embodiment in many different forms, there is shown in the drawings and will herein be described in detail at least one specific embodiment, with the understanding that the present disclosure is to be considered as an exemplification of the principles of the invention and is not intended to limit the invention to the embodiment illustrated.

As shown in the drawings, the present invention is directed to a cover assembly for multi-purpose, mobile, utility carts. The present invention is especially well suited, however, for use with carts commonly known as "crash carts," which are utilized in hospitals and similar facilities in medical emergencies, typically associated with resuscitating a patient in cardiac arrest or distress.

Figure 2:
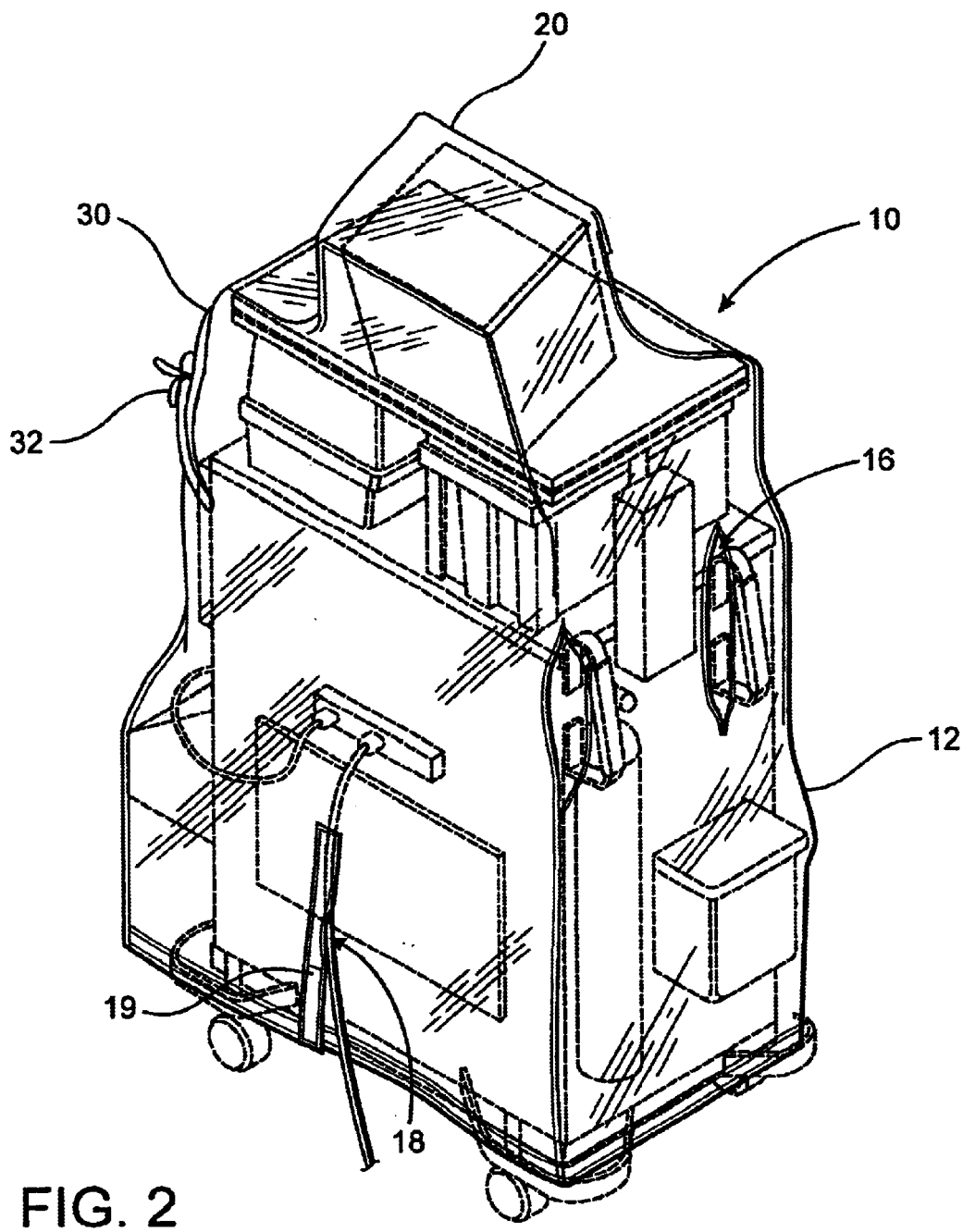
FIG. 2 is a rear perspective view of the invention illustrated in FIG. 1.

With reference now to FIGS. 1 and 2, in one embodiment the cover assembly comprises a cover generally indicated as 10, which includes a main body portion 12, a monitor portion 20, and at least one adjustable portion 30. The cover 10 is structured and disposed to be position able in an overlying relationship with the crash cart, to minimize the potential for contamination of the medical equipment and/or supplies included on the crash cart from dirt, dust, bacteria, or other typical airborne or contact contaminants. As such, the overlying relationship is at least partially defined by the cover 10 surrounding the top, front, rear, and sides of the crash cart, including the equipment and supplies contained thereon. Although it is envisioned that the present invention may be provided with a variety of lengths, widths, and heights, a preferred embodiment of the invention, as shown in FIG. 1, will include a monitor portion 20 which is approximately 23 inches by 15 inches by 14 inches, and a main body portion 12, incorporating the adjustable portion 30, which is approximately 48 inches by 23 inches by 50 inches.

Figure 3:
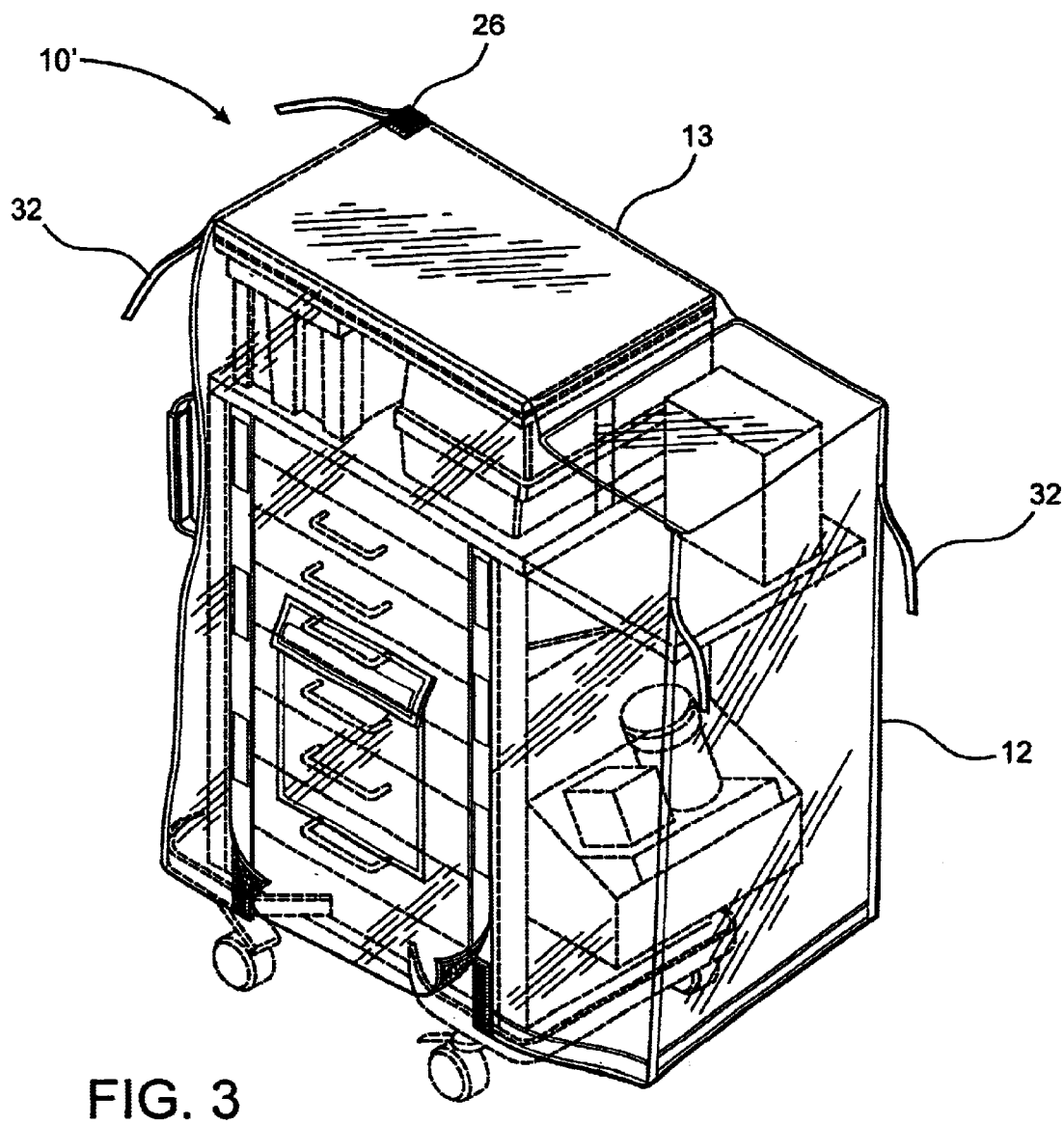
FIG. 3 is a front perspective view of a cover assembly according to the present invention in an alternative embodiment.

The main body portion 12 of the cover 10 is generally rectangular in shape and is sized in length, width and height to correspond to the length, width and height of the crash cart, as can be noted from FIGS. 1–2, as well as the embodiment of FIG. 3, which does not show a monitor portion 20. With respect to the embodiment illustrated in FIGS. 1 and 2, the monitor portion 20, is also generally rectangular in shape wherein the length, width and height generally correspond to a typical electronic, video display monitor (VIM). The monitor portion 20 is structured and disposed to at least partially overlie the electronic, video display monitor positioned on the crash cart, and ideally is cooperatively engaged with the main body portion 12 so as to provide a generally continuous composite assembly which may quickly and easily be positioned in an overlying relationship with the crash cart containing all of the equipment and supplies, including the display monitor. In one preferred embodiment, the main body portion 12 and the monitor portion 20 are at least partially constructed from a clear, flexible, tear and puncture resistant material so that the equipment and supplies on the cart are visually observable while the cart is covered, and has sufficient flexibility so as to be easily adjustable to accommodate the various combinations of equipment and supplies typically included on a crash cart. One embodiment of the present invention may comprise material such as heavy gauge, clear vinyl or plastic, although other embodiments comprising alternate materials of construction are anticipated. The cover 10 may be formed from individual panels at the top, front, rear, and sides cooperatively engaged, whether by sewn stitching, glue or other adhesive, heat sealing, etc. To form the main body portion 12, the monitor portion 20, and the adjustable portion 30. Alternatively, the entire cover 10 may be formed from a single larger panel which is formed or molded into the required configuration.

The main body portion 12 includes at least one release aperture 14. In a preferred embodiment, the main body portion 12 contains a plurality of release apertures 14. The release apertures 14 may be in the form of those illustrated in FIG. 1 by reference numeral 14, which are disposed in a generally vertical orientation originating at the bottom of the main body portion 12 and extending upward along a substantial section of the height of the main body portion 12, as illustrated in FIG. 1. The release apertures 14 are disposed in a normally closed orientation while the crash cart is not in use, so as to aid with retention of the cover assembly on the cart, thereby minimizing potential contamination of the equipment and supplies included thereon. The illustrated release apertures 14 are retained in their normally closed orientation by at least one release fastener 15, when the release fastener 15 is engaged, however, a plurality of release fasteners 15 may be included. The release fasteners 15 are further structured to allow the release aperture 14 to be disposed in an open orientation, when the release fasteners 15 are disengaged, such that the cover 10 is at least partially removable from the cart. In a preferred embodiment of the present invention, the release fasteners 15 comprise a hook and loop type of fastener to permit quick and easy disengagement when required. Alternate embodiments of the present invention may include release fasteners 15 comprising snaps, zippers, buttons, ties, or other standard fasteners.

The main body portion 12 further comprises at least one handle aperture 16, however, in a preferred embodiment, the main body portion 12 comprises a plurality of handle apertures 16 as illustrated in FIG. 2. Each handle aperture 16 is structured to permit a handle on the crash cart to extend through the cover 10 while exposing only the handle associated therewith and a minimal area of the crash cart to potential contamination. The periphery of each handle aperture 16 preferably comprises an elastic material such that each handle aperture 16 fits snug around each handle to further minimize potential contamination of the equipment and supplies included on the crash cart. A further embodiment of the present invention may comprise a handle aperture fastener to engage and close opposite sides of the handle aperture 16, after the handle has been placed there through. In yet another embodiment, the cover assembly of the present invention may comprise a release aperture in the nature of a handle aperture 16 corresponding to one or both handles and including fastener means to permit the opening of the aperture when it is necessary for personnel to engage the handles and maneuver the cart to another location, and yet, closing of the handle aperture 16 when that is not necessary, i.e., when the cart is stationary.

The main body portion 12 also comprises at least one electrical aperture 18, as illustrated in FIG. 2. As with the other release apertures 14, the electrical aperture 18 is disposed in a normally closed orientation to minimize exposure of the equipment and supplies on the crash cart to potential contamination. At least one electrical fastener 19 is provided to retain the electrical aperture 18 in its normally closed orientation. The electrical fastener 19 comprises a hook and loop type fastener in a preferred embodiment of the present invention, however, additional embodiments may comprise any standard fastener including, but not limited to, those previously disclosed. The electrical fastener 19 is structured for quick and easy disengagement so that a power supply cord may be easily connected to a power outlet to supply electricity to a component on the cart. The electrical aperture 18 may remain open if the connection to a power supply is temporary or brief, although if the connection of an electrical or power cord to an outlet is to be maintained for a period of time, the preferred form of fastener 19 permits partial closing of the electrical aperture 18, about the cord. It should be noted that the electrical aperture 18 can therefore serve as a release aperture, such that the cover 10 may be quickly and easily removed from the crash cart or at least aid in such an exercise.

As previously indicated, the cover 10 of the present invention in at least one embodiment further comprises a monitor portion 20, as illustrated in FIGS. 1 and 2. The monitor portion 20, as previously noted, is cooperatively engaged with the main body portion 12 so as to provide a generally continuous composite assembly. In one embodiment, the monitor portion 20 may be connected to the top of the main body portion 12 near the center of the front, as illustrated in FIGS. 1 and 2. An alternate embodiment of the present invention provides for the monitor portion 20 to be connected to the top of the main body portion 12 centered along the side opposite the adjustable portion 30. In this alternate embodiment, the invention will include a monitor portion 20 which is approximately 23 inches by 15 inches by 14 inches, and a main body portion 12, incorporating the adjustable portion 30, which is approximately 49 inches by 23 inches by 50 inches.

The monitor portion 20 is structured and disposed to be quickly and easily position able in an at least partially overlying relationship with an electronic, video display monitor positioned on the crash cart. The monitor portion 20 preferably includes a release aperture in the form of a monitor aperture 22, which is disposed in a normally closed orientation. In one embodiment of the present invention, at least one monitor fastener 24 is provided to retain the monitor aperture 22 in the normally closed orientation. The monitor fastener 24 is further structured to allow the monitor aperture 22 to be selectively position able between an at least partially open orientation to permit medical personnel to access and/or operate the electronic display monitor, without removing the entire cover 10 from an overlying relationship with the crash cart, and the normally closed orientation. The monitor fastener 22, in a preferred embodiment, comprises a hook and loop type of fastener. However, as with the fasteners previously noted, additional embodiments of the present invention may comprise any of the previously disclosed standard fasteners as a monitor fastener 22.

The present invention preferably also includes at least one adjustable portion 30 which is integrally formed with the main body portion 12. There are numerous combinations of equipment and/or supplies which may be included on the crash cart depending on its specific intended use, and, therefore, a cover 10 comprising a single configuration may not be suitable for each possible combination, and it is to be understood that the present invention may therefore, assume other embodiments, such as that shown in FIG. 3, but not limited thereto. In one embodiment, the adjustable portion 30 is structured and disposed to provide a quick and easy means to assure a proper fit of the cover 10 over a majority of the possible crash cart configurations as a proper fit is ideal to minimize air circulation under the cover 10, thereby minimizing potential contamination of the equipment and supplies included on the crash cart. FIG. 1 shows the adjustable portion 30 in a fully expanded orientation, as required to accommodate a movable shelf on the cart, which is shown in an open, upright position. FIG. 2 illustrates the adjustable portion 30 in an at least partially collapsed orientation, to provide a proper fit around the movable shelf which is shown in a closed, folded position. The adjustable portion 30 of this embodiment may comprise at least one, but preferably a plurality of retention members, which in a preferred embodiment comprise ties 32, as illustrated in FIG. 1. Each tie 32 has a free distal end 34, and a secure proximate end 35, which is secured to the adjustable portion 30. The ties 32 remain in a free and disengaged position when the adjustable portion 30 is in an open orientation, as illustrated in FIG. 1. As the adjustable portion 30 is collapsed to assure a proper fit around the crash cart, the ties 32 are structured to secure the excess material of the adjustable portion 30 against the crash cart, such that the ties 32 retain the adjustable portion 30 in an at least partially collapsed orientation when operatively engaged, so as to prevent the excess material from flapping about and becoming entangled with foreign objects as the crash cart is transported from location to location. While FIGS. 1 and 2 illustrate the adjustable portion 30 in either an open orientation or an at least partially collapsed orientation, respectively, it is envisioned that the adjustable portion 30 may encompass other orientations besides those illustrated.

A preferred embodiment of the present invention further comprises a pouch 40 disposed on an exterior surface of the cover 10, as illustrated in FIG. 1. The pouch 40 further comprises a flap 42, which may be secured to the pouch 40 by pouch fastener 44. The pouch fastener 44 may comprise any one of the standard fasteners previously disclosed, however, a hook and loop type fastener is provided in a preferred embodiment. In at least one embodiment, the pouch 40 is of sufficient size to completely contain a standard size medical chart, so that important patient information is readily available to medical personnel if required in an emergency situation. In addition, the pouch 40 may be utilized to store pertinent information about the equipment and/or supplies included on the crash cart including, for example, an inventory of equipment and supplies, a log of diagnostic equipment tests required and/or performed, routine maintenance, supply restocking dates, or any other information deemed necessary by medical personnel. The cover assembly could be provided, of course, with more than one pouch to accommodate both a medical chart an listing of equipment carried on the cart, etc.

As noted above, there are different variations of "crash carts." For example, some crash carts are know as a "two box" version with a video display monitor positioned centrally thereon whereas others are known as a "modern" version with the video display monitor assuming a position more towards one forward end of the cart. The inventive cover assembly has been described herein as accommodating both versions, with possible variations in the dimension thereof, as well. As another example, some crash carts may not carry a video display monitor at all and/or a light-weight transportable lap-top computer may be utilized instead. As such, and with reference momentarily to FIG. 3, it is emphasized that the cover assembly of the present invention can assume alternative embodiments, such as cover 10' shown therein, wherein a top portion 13 does not include a monitor portion 20. In this and other embodiments, the cover assembly may include a top portion aperture 26 formed at an end thereof to accommodate the use of equipment such as a pole for holding intravenous (IV) fluids, a holder for the cables of defibrillators or other shock equipment, and the like. Additionally, as illustrated in the embodiment of FIG. 3, the top portion 13 of the cover 10' may include retention members, preferably ties 32, disposed at each corner. The ties 32 allow the cover 10' to be secured in place about the crash cart, while the top portion 13 is disposed in a partially open orientation. Of course, the cover assembly of the present invention can be modified from that shown in the drawings to accommodate these and other versions of crash carts which may exist now or which later become known.

Since many modifications, variations and changes in detail can be made to the described preferred embodiment of the invention, it is intended that all matters in the foregoing description and shown in the accompanying drawings be interpreted as illustrative and not in a limiting sense. Thus, the scope of the invention should be determined by the appended claims and their legal equivalents.

Now that the invention has been described,

What is claimed is:

1. A cover assembly for a cart comprising:

a cover, said cover including a main body portion and at least one adjustable portion, said cover further comprising a monitor portion, said monitor portion structured and disposed to at least partially overlie a display monitor positioned on the cart, said cover structured to be position able in an overlying relationship with the cart, and at least one release aperture on said cover, wherein said cover is at least partially removable from the cart when said release aperture is disposed in an open orientation.

2. An assembly as recited in claim 1 wherein said cover is at least partially constructed of clear, flexible material.

3. An assembly as recited in claim 1 wherein said at least one release aperture is disposed on said main body portion, said release aperture having a normally closed orientation.

4. An assembly as recited in claim 3 further comprising at least one release fastener, said release fastener structured to retain said at least one release aperture in said normally closed orientation when said release fastener is engaged.

5. An assembly as recited in claim 4 wherein said release aperture is disposable into an open orientation when said release fastener is disengaged.

6. An assembly as recited in claim 1 comprising a plurality of release apertures.

7. An assembly as recited in claim 6 wherein at least one of said plurality of release apertures comprises an electrical aperture disposed on said cover, said electrical aperture disposed in a normally closed orientation by at least one electrical fastener.

8. An assembly as recited in claim 7 wherein said electrical aperture is position able into an open orientation when said electrical fastener is disengaged.

9. An assembly as recited in claim 6 wherein at least one of said plurality of release apertures comprises a monitor aperture on said monitor portion, said monitor aperture disposed in a normally closed orientation by at least one monitor fastener.

10. An assembly as recited in claim 9 wherein said monitor aperture is selectively position able between an at least partially open orientation and said normally closed orientation.

11. An assembly as recited in claim 1 wherein said at least one adjustable portion comprises at least one retention member structured and disposed to retain said adjustable portion in an at least partially collapsed orientation when said retention member is operatively engaged.

12. An assembly as recited in claim 11 wherein said at least one retention member comprises a pair of ties.

13. An assembly as recited in claim 1 further comprising a pouch disposed on an exterior surface of said cover.

14. An assembly as recited in claim 1 wherein said overlying relationship is at least partially defined by said cover surrounding the top, front, rear, and sides of the cart.

15. A cover assembly for a cart comprising:

a cover, said cover having a main body portion comprising at least one release aperture disposed on said main body portion, at least one release fastener structured to retain said release aperture in a normally closed orientation when said release fastener is engaged, said release aperture disposable into an open orientation when said release fastener is disengaged, a monitor portion structured and disposed to at least partially overlie a display monitor positioned on the cart, a monitor aperture on said monitor portion selectively position able between an at least partially open orientation and a normally closed orientation, at least one adjustable portion having at least one retention member structured to retain said adjustable portion in an at least partially collapsed orientation when said retention member is operatively engaged, and said cover structured to be position able in an overlying relationship with the cart.

* * * * *